United States Patent [19]

Kim et al.

[11] Patent Number: 5,681,823
[45] Date of Patent: Oct. 28, 1997

[54] $P^1$, $P^4$-DITHIO-$P^2$-$P^3$-MONOCHLOROMETHYLENE 5', 5'''-DIADENOSINE $P^1$, $P^4$-TETRAPHOSPHATE AS ANTITHROMBOTIC AGENT

[75] Inventors: Byung K. Kim, Cumberland, R.I.; Paul C. Zamecnik, Shrewsbury, Mass.

[73] Assignee: PRP Inc., Watertown, Mass.

[21] Appl. No.: 643,029

[22] Filed: May 2, 1996

[51] Int. Cl.$^6$ ............................................. A61K 31/70
[52] U.S. Cl. .................................. 514/47; 514/822
[58] Field of Search ............................. 514/47, 822

[56] References Cited

U.S. PATENT DOCUMENTS 5,049,550  9/1991  Zamecnik .................................. 514/47

OTHER PUBLICATIONS

Zamecnik, P., et al., "Analogues of diadenosine 5',5'''-$P^1$, $P^4$-tetraphosphate (Ap$_4$A) as potential antiplatelet-aggregation agents"; Proc. Natl., Acad. Sci. USA 89:2370–2373 (1992).

Byung, K., et al., "Antithrombotic effect of β,β'-monochloromethylene diadenosine 5', 5'''-$P^1$, $P^4$-tetraphosphate"; Proc. Natl. Acad. Sci. USA 89:11056–11058 (1992).

Humphries, R., et al., "A novel series of $P_{2T}$ purinoceptor antagonists: definition of the role of ADP in arterial thrombosis"; Trends in Pharmaceutical Sci. 16:179–181 (1995).

Blackburn, G., et al., "Synthetic Structural Analogues of Dinucleoside Polyphosphates";McLennan, A. (ed.), Ap$_4$A and Other Dinucleoside Polyphosphates; CRC Press, Inc., Boca Raton, U.S.A.; Chapter 11 305–343 (1992).

Blackburn, G., et al., "Synthesis and resistance to enzymic hydrolysis of stereochemically-defined phosphonate thiophosphate analogues of $P^1$, $P^4$-bis (5'-adenosyl) tetraphosphate"; Nucleic Acids Research 14(17):6991–7004 (1987).

Eibl, J. et al., 124:37715s "Stable preparation for the treatment of blood coagulation disorders comprising an activated coagulation factor and lipid vesicles";CA Selects: Phospholipids (Chemical Aspects) Issue 3 (1996) Abstract.

Eibl, J. et al., 124:37716t "Stable preparation for the treatment of blood coagulation disorders comprising an activated coagulation factor and lipid vesicles";CA Selects: Phospholipids (Chemical Aspects) Issue 3 (1996) Abstract.

Byung, K. et al., "Diadenosine Tetraphosphate Analogues—Antiplatelet Effects"; SBIR I Grant Application Abstract, submitted Apr. 12, 1994.

Byung, K. et al., "Diadenosine Tetraphosphate Analogue—Antithrombotic Effect": SBIR II Grant Application Abstract, submitted Dec. 12, 1995.

Byung, K. et al., "Diadenosine Tetraphosphate Analogue—Antiplatelet Effects": SBIR Grant Abstract Project No. 1 R43 HL53864-01, submitted Apr. 12, 1994.

*Primary Examiner*—Kimberly Jordan
*Attorney, Agent, or Firm*—Wolf, Greenfield & Sacks, P.C.

[57] ABSTRACT

A novel composition, $P^1$, $P^4$-dithio-$P^2$, $P^3$-monochloromethylene 5', 5'''-diadenosine $P^1$, $P^4$-tetraphosphate, is disclosed. The composition is useful as a therapeutic agent for prevention of thrombosis and for modulating a thrombolytic effect in a mammal.

14 Claims, No Drawings

$P^1$, $P^4$-DITHIO-$P^2$-$P^3$-MONOCHLOROMETHYLENE 5', 5'''-DIADENOSINE $P^1$, $P^4$-TETRAPHOSPHATE AS ANTITHROMBOTIC AGENT

GOVERNMENT SUPPORT

Work described herein was supported in part by NIH Grant IR43HL53864-01 (AHR-B1)

BACKGROUND OF THE INVENTION

Intravascular clotting is a common disorder. One of the most common of such disorders is the formation of thrombi in an arterial blood vessel which remain at the point of formation. Thrombi can have serious adverse effects on an individual. For example, thrombus formation in the heart artery can restrict blood flow, resulting in myocardial infarction (death of the heart muscle), which is one of the most severe forms of heart attacks.

Thrombosis in arterial blood vessels and prosthetic medical devices is characterized by the adhesion of platelets to the damaged vessel wall or prosthetic surface, the release of their granular content, the synthesis of prostaglandin endoperoxides and platelet aggregation. The newly formed platelet aggregate is a fragile clump, a so called "white thrombus". The exposure of procoagulant activity on the surface of aggregated (activated) platelets triggers the formation of a fibrin network on the white thrombus and stabilizes it. Various antiplatelet agents have been studied for many years as potential targets for beneficial clinical inventions with respect to the inhibition of thrombus formation. Some agents such as aspirin and dipyridamole have come into use as prophylactic antithrombotic agents, and others have been the subjects of clinical investigations. To date, the powerful agents such as disintegins, ticlopidine and its analogues have substantial side effects, while the more benign agents such as aspirin have useful but limited effectiveness (Hass, W. K., et at., *N Engl J Med*, 321: 501–507, (1989); Weber, M. A. J., et at., *Am.J. Cardiol.*, 66:1461–1468 (1990); Lekstrom, J. A., Bell, W. R. *Medicine*, 70:161–177 (1991)). Where information is available, clinical efficacy of the newer drugs, such as ReoPro (7E3), is impressive, but the success of recent trials has been complicated with the finding that these approaches have been associated with an increased risk of major bleeding, sometimes necessitating blood transfusion (*The EPIC Investigators* (1994) *New Engl. J. Med.*, 330: 956–961). Thus, it would appear that the ideal "benefit/risk" ratio (that is, improved efficacy over that of aspirin compared with the propensity to cause unwanted bleeding) has not been achieved.

Recent studies on more potent and selective compounds for inhibition of platelet aggregation suggests greater benefit in their antithrombotic efficacy. A number of studies have suggested that ADP, a common agonist, plays a key role in the initiation and progression of arterial thrombus formation (Bernat, A., et at., *Thromb. Haemost.*, 70:812-126 (1993); Maffrand, J. P., et al., *Thromb. Haemostas*, 59:225–230 (1988); Herbert, J. M., et at., *Arteriosclerosis and Thrombosis*, 13:1171–1179 (1993)). A potent inhibitor of ADP-induced platelet aggregation would therefore, be of particular interest in searching antithrombotic agents. It has been known for some time that diadenosine 5', 5'''-$P^1$,$P^4$-tetraphosphate ($AP_4A$) is a competitive inhibitor of ADP-induced platelet aggregation (Zamecnik, P. C., et al., *Proc. Nat'l. Acad. Sci. USA*, 89:2370–2373 (1992); Harrison, M. J., et at., *FEBS Lett.*, 54(1): 57–60 (1975); Luthje, J., et at., *Biochem. Biophys. Res. Comm.*, 118:704–709 (1984); Chao, F. C., et at., *Hoppe Seyler's Z Physiol. Chem.*, 365:610 (1984).

The dinucleotide, $AP_4A$, is an ubiquitous component of living cells (Zamecnik, P. C. and Stephenson, M. L., Regulatory mechanisms for protein synthesis, In: *Mammalian Cells*, San Pietro, A., Lamborg, M. R. and Kenney, P. C. (eds.), Academic Press, New York, pp. 3–16 (1967)). $AP_4A$ is present in normal human platelets in a concentration higher than that present in any other cellular compartment (Flodgaard, M. and Klenow, M., *Biochemical Journal* 208:737–742 (1983)). The stored $AP_4A$ was thought to be metabolically inert because incubation of platelets with $^3$H-adenosine results in labeled ATP but not labeled $AP_4A$. Thrombin treatment of platelets induces the complete release of $AP_4A$, along with other storage pool nucleotides, including ADP and the dinucleotide, diadenosine 5', 5'''-$p^1$, $p^3$-triphosphate ($AP_3A$) (Luthje, J. and Oglivie, A., *Biochem. Biophys. Res. Comm.* 115:252–260 (1983)). $AP_3A$ is hydrolyzed in plasma to AMP (adenosine monophosphate) and ADP (adenosine diphosphate); $AP_4A$ is degraded to AMP and ATP (adenosine triphosphate) (Luthje, J. and Oglivie, A., *European Journal of Biochemistry* 149:119–127 (1985)).

The precise physiological role of $AP_4A$ has not been defined, but it has been associated with a variety of cellular metabolic events, Zamecnik, P., *Annals. of Biochemistry* 134:1–10 (1983). The unusually high concentration of $AP_4A$ in platelets has led to speculation that it has a role in platelet physiology. Platelets stimulated to undergo aggregation show a second phase of aggregation upon the release of endogenous ADP stored in the dense granules. In vitro experiments have demonstrated that $AP_4A$ competitively inhibits ADP-induced platelet aggregation, causing an immediate dispersion of aggregated platelets, even when aggregation has progressed to 60% completion (Chao F. C. and Zamecnik, P., *Hoppe Seyler'S Z. Physiol. Chem.* 365:610 (1984)). By contrast, $AP_3A$ causes a gradual aggregation of platelets, most likely through its degradation product, ADP. The aggregation activity of $AP_3A$ is immediately reversible upon the addition of $AP_4A$ (Luthje, J. and Oglivie, A., *Biochem. Biophys. Res. Comm.* 118:704–709 (1984)).

Although the process of thrombus formation is only incompletely understood, two major stages have been identified: the aggregation of platelets at the site of an arterial blood vessel lesions and the formation of cross-linked fibrin polymer which binds the developing clot together.

U.S. Pat. No. 5,049,550 issued to P. C. Zamecnik on Sep. 17, 1991 (hereinafter "Zamecnik '550") describes the use of $AP_4A$ and analogs of $AP_4A$ as antithrombotic agents in, for example, the prevention of coronary and cerebral vascular thromboembolic events, and in the prevention of thrombosis and hemodialysis arteriovenous shunts. The Zamecrdk '550 patent also describes methods for the prevention of thrombi formation which rely upon the inhibition of platelet aggregation and related compositions which contain an $AP_4A$ analog alone, or in conjunction with, a thrombolytic agent. In particular, Zamecnik '550 report the inhibitory effects ($ID_{50}$) of various $AP_4A$ analogs on ADP-induced platelet aggregation as one measure of the antithrombotic effect of these agents. The substitution of a chlorine for a fluorine in the biphosphonate analog of $AP_4A$ having a P-C-P bridge located in the $P_2$, $P_3$ position did not appear to have a substantial effect on inhibitory activity of the analog in the ADP-induced platelet aggregation assay.

SUMMARY OF THE INVENTION

This invention is based on the discovery that $P^1$, $P^4$-dithio -$P^2$-$P^3$ monochloromethylene 5', 5''' diadenosine $P^1$, P⁴-tetraphosphate (alternatively referred to herein as "thio-CHCl-AP₄A" or "Ap$_s$pCHClpp$_s$A") has a more potent ADP-induced platelet aggregation inhibitory effect compared to the inhibitory effects observed for the other AP₄A analogs previously disclosed in Zamecnik '550. Accordingly, this invention relates to compositions containing Ap$_s$pCHClpp$_s$A and the use of such compositions in the prevention of coronary and cerebral vascular thrombosis and hemodialysis arteriovenous shunts and the prevention of thrombi formation. The invention further relates to compositions containing Ap$_s$pCHClpp$_s$A for therapeutic use, alone or in conjunction with a thrombolytic agent.

According to one aspect of the invention, a composition containing Ap$_s$pCHClpp$_s$A is disclosed. In accordance with a particularly preferred embodiment, Ap$_s$pCHClpp$_s$A is present, together with a pharmaceutically acceptable carrier, in an effective antithrombotic amount. In general, an effective antithrombotic amount is an amount effective for inhibiting platelet aggregation.

According to another aspect of the invention, a pharmaceutical composition is provided. The composition contains Ap$_s$pCHClpp$_s$A and a pharmaceutically acceptable carrier. In a particularly preferred embodiment, the pharmaceutical composition contains an amount Ap$_s$pCHClpp$_s$A for modulating a thrombolytic effect in a mammal. Thus, in the preferred embodiment, the pharmaceutical composition is formulated to contain a preselected amount (e.g., a single dose) of Ap$_s$pCHClpp$_s$A for administration to the mammal.

According to yet another aspect of the invention, a pharmaceutical composition containing Ap$_s$pCHClpp$_s$A, together with a thrombolytic amount of at least one thrombolytic agent is disclosed herein. Preferably, Ap$_s$pCHClpp$_s$A is present in the composition in an effective antithrombotic amount. More preferably, the thrombolytic agent is selected from the group of agents consisting of tissue plasminogen activator, streptokinase and urokinase.

Methods for modulating a thrombolytic effect in a mammalian in need of such modulation also are disclosed herein. The methods involve administering to the mammal a pharmaceutical composition containing an effective amount of Ap$_s$pCHClpp$_s$A to modulate the thrombolytic effect. According to one embodiment, the method for modulating a thrombolytic effect involves dissolving a thrombus in the mammal. The effective amount of Ap$_s$pCHClpp$_s$A that is necessary to modulate the thrombolytic effect is an effective antithrombotic amount. Preferably, the Ap$_s$pCHClpp$_s$A is administered to the mammal together with an effective thrombolytic amount of a thrombolytic agent. Preferred thrombolytic agents are selected from the group consisting of tissue plasminogen activator, streptokinase and urokinase. As will be immediately apparent to one of ordinary skill in the art, Ap$_s$pCHClpp$_s$A can be administered to the mammal at the same time or sequential with the administration to the mammal of an effective thrombolytic amount of the thrombolytic agent.

According to yet another embodiment, the method for modulating a thrombolytic effect in a mammal involves inhibiting the growth of a thrombus in the mammal. The effective amount of Ap$_s$pCHClpp$_s$A necessary to inhibit the growth of the thrombus is an amount effective for inhibiting platelet aggregation or an effective antithrombotic amount.

According to yet another embodiment, the method for modulating a thrombolytic effect in the mammal involves reducing (e.g., preventing) the formation of a thrombus in the mammal. The formation of a thrombus in a mammal can be reduced by administering to the mammal an effective antithrombotic amount of Ap$_s$pCHClpp$_s$A or by administering an amount of Ap$_s$pCHClpp$_s$A that is effective for inhibiting platelet aggregation. Although Applicants do not intend to limit the invention to one particular mechanism for reducing thrombus formation, it is believed that the formation of a thrombus in the mammal is reduced by inhibiting platelet aggregation and that the administration to the mammal of an effective amount of Ap$_s$pCHClpp$_s$A inhibits platelet aggregation thereby reducing or preventing the formation of the thrombus.

According to yet another embodiment of a method for modulating a thrombolytic effect in a mammal, an effective amount of Ap$_s$pCHClpp$_s$A for inhibiting platelet aggregation is administered to the mammal to inhibit platelet aggregation in vivo.

These and other aspects of the invention, as well as various advantages and utilities, will be more apparent with reference to the detailed description of the preferred embodiments.

Each of the patents, patent publications and references identified in this document are incorporated in the entirety herein by reference.

DETAILED DESCRIPTION OF THE INVENTION

The subject invention relates to the use of Ap$_s$pCHClpp$_s$A as an antithrombotic agent. The invention is based on the discovery that the administration of Ap$_s$pCHClpp$_s$A to a mammal inhibits platelet aggregation and presumably thereby reduces the incidence of thrombosis. Surprisingly, the in vitro platelet aggregation inhibitory activity of Ap$_s$pCHClpp$_s$A is nearly an order of magnitude greater than the inhibitory activity of naturally-occurring AP₄A and is significantly greater than the activities of known AP₄A analogs (e.g., compound E₃ as disclosed in Zamecnik '550, which differs from Ap$_s$pCHClpp$_s$A in having a fluorine rather than a chlorine at the methylene bridge). Ap$_s$pCHClpp$_s$A also has a significantly greater platelet aggregation inhibitory activity than that of its corresponding non-thio counterpart (compound E₁₀ as disclosed in Zamecnik '550. See also the Examples herein). This substantial increase in platelet aggregation inhibitory activity could not have been predicted based on structural similarity to AP₄A or known AP₄A analogs (the structures of which are provided below). For example, Zamecnik '550 (Table 3) shows that the inhibitory effect (ID$_{50}$ value) for AppCHClppA (compound E₁₀) is 3 μM, and the ID$_{10}$ value for AppCHFppA (compound E₅) is 4 μM. Thus, for these AP₄A analogs, the substitution of chlorine for fluorine had little effect on ADP-induced platelet aggregation inhibitory activity. In view of these results, one skilled in the art would not have expected substantially improved inhibitory activity for the invention compared to AP₄A analogs of the prior art.

Naturally-occurring AP₄A has the following formula ("Formula I"):

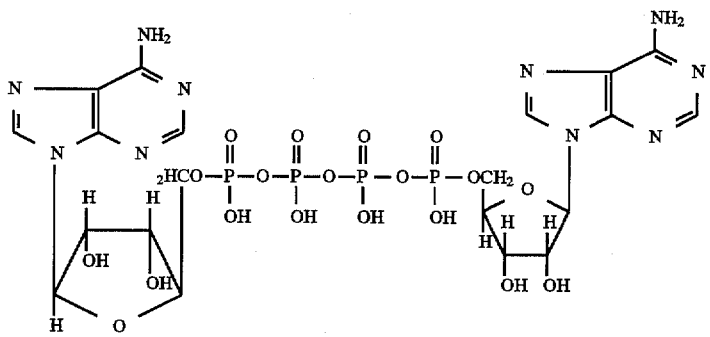

The Zamecnik '550 E$_5$ composition (abbreviated AppCHFppA) has the following formula:

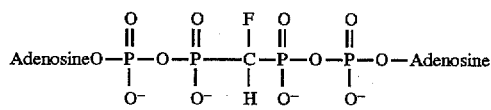

The Zamecnik '550 E$_{10}$ composition (abbreviated AppCHClppA) has the following formula:

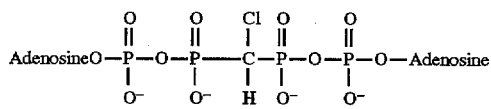

The Zamecnik '550 E$_{13}$ composition (abbreviated Ap$_s$pCHFpp$_s$A) has the following formula:

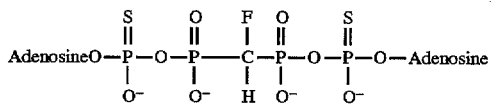

The newly disclosed AP$_4$A analog, Ap$_s$pCHClpp$_s$A, has the following formula:

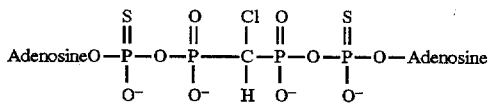

AP$_4$A has been shown to inhibit markedly ADP-induced platelet aggregation when it is administered to a mammal. Added before or during aggregation, exogenous AP$_4$A blunts the secondary wave response and causes rapid dispersion of aggregated platelets. The magnitude of inhibition has been shown to bear a direct relationship to the dose of exogenous AP$_4$A. Because platelet plugs form the bull of arterial thrombi, a preferred therapeutic strategy to prevent thrombosis is to utilize a therapeutic agent (e.g., AP$_4$A) that interferes with the adherence of platelets to each other and presumably, to vessel walls as well. Thus, in one embodiment of the invention, Ap$_s$pCHClpp$_s$A is administered to a mammal to modulate a thrombolytic effect in the mammal, e.g., to prevent or inhibit restenosis.

As used herein, "modulating a thrombolytic effect" refers to preventing or reducing the incidence of thrombosis in a mammal, e.g., statistically reducing the likelihood of thrombus formation and growth relative to the likelihood of thrombus formation/growth in the absence of thio-CHCl-AP$_4$A administration. For example, modulating a thrombolytic effect in a mammal embraces (1) facilitating dissolving a thrombus in the mammal; (2) inhibiting the growth of a thrombus in the mammal; (3) reducing (e.g., preventing) the formation of a thrombus in the mammal; and (4) inhibiting platelet aggregation in the mammal (e.g., for prophylactic applications where it is desirable to reduce the likelihood of thrombus formation).

AP$_4$A has a short half-life in rabbit blood, both in vive and ex vive (platelets obtained from the blood of subjects who have received AP$_4$A). Compared to in vive clearance, the ex vivo decay of AP$_4$A is significantly longer. This may be explained by the use of titrated blood, which has been shown to inhibit the metal ion dependent hydrolase responsible for the catabolism of AP$_4$A (Luthje, J. and Ogilvie, A., European J. Bio. Chem. 149:119–127 (1995)) and is consistent with the observation that 90% of $^{32}$P-labeled AP$_4$A added to normal plasma is degraded in ten minutes when incubated at 37° C. (Kim et al., Blood 66:735–737 (1995)). Endogenous platelet AP$_4$A, released in relatively high concentrations from dense granules when stimulated platelets undergo the release phenomenon may be important in modulating local platelet aggregation-dispersion. Thus, as described in U.S. Pat. No. 5,049,550 (Zamecnik '550), an antithrombotic effect can be obtained by maintaining a high circulating AP$_4$A level via the administration of exogenous AP$_4$A. This suggests that AP$_4$A or an analog thereof, such as Ap$_s$pCHClpp$_s$A, can be used as a clinical anti-platelet, antithrombotic agent.

According to one aspect of the invention, a method for modulating a thrombolytic effect in a mammal in need thereof is provided. The method for modulating the thrombolytic effect involves administering to the mammal a pharmaceutical composition containing an effective amount of Ap$_s$pCHClpp$_s$A to modulate the thrombolytic effect. As used herein, modulating a thrombolytic effect embraces facilitating dissolution of a thrombus in the mammal, inhibiting the growth of an existing thrombus in the mammal, reducing (e.g., preventing) the formation of a thrombus, and inhibiting platelet aggregation (in the presence or absence of a pre-existing thrombus).

In general, Ap$_s$pCHClpp$_s$A can be administered intraperitoneally, intramuscularly, orally, gastrointestinally, subcutaneously or via slow release encapsulation. However, a preferred method of administration to the mammal is by intravenous injection. Ap$_s$pCHClpp$_s$A is introduced into the bloodstream of the mammal at any convenient point, although injection upstream from and near to the site of the suspected or known thrombus is preferred. The effective amount of Ap$_s$pCHClpp$_s$A for modulating the thrombolytic effect in the mammal is that quantity which will mediate the particular thrombolytic effect in the mammal for which the mammal is being treated. For example, where the method for modulating a thrombolytic effect is facilitating dissolution of a thrombus in the mammal, the effective amount of $Ap_spCHClpp_sA$ to modulate this thrombolytic effect is an effective anti-thrombotic amount, i.e., that quantity which, in combination with an antithombolytic agent, will facilitate the dissolution of a pre-existing thrombus. Preferably, the effective antithrombotic amount is between about 5 mg and 25 mg per kg body weight. More preferably, the effective antitrombotic amount is between about 10 mg and 15 mg per kg body weight.

Where the method for modulating a thrombolytic effect is for inhibiting the growth of a thrombus in the mammal, the effective amount of the $Ap_spCHClpp_sA$ is that quantity of $Ap_spCHClpp_sA$ which is effective for inhibiting platelet aggregation in vivo (5–25 mg per kg body weight per day, more preferably between 10–15 mg per kg per day). In general, the amount effective for inhibiting platelet aggregation in vivo is between about 5 mg and 25 mg per kg body weight, more preferably, between about 10 mg and 15 mg per kg body weight.

Where the method for modulating a thrombolytic effect is for reducing the formation of a thrombus in the mammal (e.g., by inhibiting platelet aggregation in vivo), then the effective amount of $Ap_spCHClpp_sA$ to achieve this objective is an amount of $Ap_spCHClpp_sA$ which will inhibit platelet aggregation in vivo and, presumably, thereby reduce (e.g., prevent) the formation of a thrombus in the mammal. Where the method for modulating a thrombolytic effect is for inhibiting platelet aggregation in the mammal (in the presence or absence of a thrombus), the effective amount of $Ap_spCHClpp_sA$ is approximately the same amount of $Ap_spCHClpp_sA$ effective for inhibiting platelet aggregation in vivo.

The actual quantity of $Ap_spCHClpp_sA$ given in a specific instance for achieving the above objectives will vary according to the particular compositions formulated, the method of administration and the clinical needs of the patient. However, in general, the dosage of $Ap_spCHClpp_sA$ is in the range of 10 μg to 10 mg/kg/day.

As noted above, the effective dose for inhibiting platelet aggregation in vivo is approximately the same as the effective dose for inhibiting thrombosis ("an effective antithrombotic amount"). However, in vivo intravascular clot formation (thrombosis) is the result of a complex process involving a series of patho-physiological events, including for example, 1) platelet activation, aggregation, and activation of the coagulation system (thrombin generation) following platelet adhesion to the injured blood vessel wall;
2) release by the injured blood vessel of tissue coagulation factor (thrombin generation through the extrinsic coagulation pathway);
3) release by the injured blood vessel of tissue plasminogen activator (plasmin generation);
4) antithrombin activity (associated with normal physiological activity); and
5) enhanced platelet interaction with subendothelial tissues and shearing off of loose clots by the blood stream. Collectively, these events result in thrombosis, although some of these events serve to form clots and other events prevent clot formation. Accordingly, in a preferred embodiment, $Ap_spCHClpp_sA$, is administered in combination with an antithrombin agent, such as heparin, the most commonly used antithrombin agent.

$Ap_spCHClpp_sA$ can be administered by injection in conjunction with a pharmaceutically-acceptable carrier, either alone or in combination with another drag (e.g., a thrombolytic agent). Pharmaceutically-acceptable carriers are those which dissolve $Ap_spCHClpp_sA$ or hold it in suspension and which are compatible with physiological conditions. Examples of pharmaceutically-acceptable carriers are aqueous solutions of salts or non-ionic compounds such as sodium chloride or glucose, generally at an isotonic concentration. Although other drugs may be present in the solution with $Ap_spCHClpp_sA$, it is important that such additional components not interfere with the ability of $Ap_spCHClpp_sA$ to inhibit platelet aggregation in vivo. Those skilled in the art will know, or will be able to ascertain with no more than routine experimentation, particular pharmaceutically-acceptable carriers for $Ap_spCHClpp_sA$. Further, those skilled in the art will know, or will be able to ascertain with no more than routine experimentation, whether other drags can be present in the solution with $Ap_spCHClpp_sA$ without interfering with the ability of $Ap_spCHClpp_sA$ to inhibit platelet aggregation in vivo. The compositions for modulating a thrombolytic effect are useful for treating any mammal, including, but not limited to, humans, domestic animals and farm animals.

According to a particularly preferred embodiment of the invention, a method for modulating a thrombolytic effect in a mammal involves facilitating dissolution of a thrombus in the mammal or preventing its extension. Preferably, the method for dissolving the thrombus involves administering to the mammal an effective antithrombotic amount of $Ap_spCHClpp_sA$ together with an effective thrombolytic amount of a thrombolytic agent. As used herein, "thrombolytic agent" refers to an agent which breaks up or dissolves a thrombus. A thrombus refers to a clot in the cardiovascular system that is formed from constituents of blood; it may be occlusive or attached to the vessel or heart wall without complete obstruction of the lumen. Thus, an effective thrombolytic amount of the thrombolytic agent is that quantity which will dissolve a clot in vivo. Those skilled in the art will know, or will be able to ascertain with no more than routine experimentation, the effective antithrombotic amounts of $Ap_spCHClpp_sA$ as well as the effective thrombolytic amounts of the thrombolytic agent. In the particularly preferred embodiments, the thrombolytic agent is selected from the group consisting of tissue plasminogen activator, streptokinase and urokinase.

$Ap_spCHClpp_sA$ can be coadministered with the thrombolytic agent to the mammalian recipient. For the purposes of this invention, "coadministering" embraces (1) the simultaneous administration of $Ap_spCHClpp_sA$ and the thrombolytic agent and (2) the administration of $Ap_spCHClpp_sA$, shortly before or after the administration of the thrombolytic agent. Administration of $Ap_spCHClpp_sA$ in this manner results in dispersion and/or prevention of the reaggregation of platelets that are released from the blood clot in response to the action of the thrombolytic agent. Since $Ap_spCHClpp_sA$ acts at a very early stage in thrombus formation, $Ap_spCHClpp_sA$ is particularly useful when combined with one or more clot-dissolving drugs, such as those described above.

According to yet another embodiment of the invention, the method for modulating a thrombolytic effect involves inhibiting the growth of an existing thrombus in the mammal. According to this embodiment, the effective amount of $Ap_spCHClpp_sA$ which is administered is an amount which is effective for inhibiting platelet aggregation in vivo (an "effective" antithrombotic amount). Although Applicants do not intend that the invention be limited to a particular mechanism, it is believed that the inhibition of growth of the thrombus is accomplished by preventing the further aggregation of platelets at the periphery of the existing thrombus.

According to yet another embodiment of the invention, the method for modulating a thrombolytic effect involves reducing the formation of a thrombus in the mammal. It is believed that administration of $Ap_spCHClpp_sA$ inhibits formation of the thrombus in the mammal by preventing platelet aggregation in vivo. Accordingly, the effective amount of $Ap_spCHClpp_sA$ for reducing (e.g., preventing) the formation of the thrombus in the mammal is an amount effective for inhibiting platelet aggregation in vivo. Thus, $Ap_spCHClpp_sA$ is particularly useful in the prevention of coronary and cerebral vascular thrombotic events. Moreover, because thrombi occur primarily in the arterial system, a preferred use of $Ap_spCHClpp_sA$ is in the treatment of patients with a high risk of arterial thrombi in the heart and brain. In addition, $Ap_spCHClpp_sA$ is useful in hemodialysis, in which patients are linked to artificial kidney machines, for the purpose of preventing thrombosis in arterial venous shunts. Further, it is believed that $Ap_spCHClpp_sA$ is useful as a secondary prophylactic agent for the purpose of preventing the reoccurrence of myocardial infarctions and/or strokes when present in an mount sufficient to inhibit platelet aggregation. Thus, in general, the effective mount of $Ap_spCHClpp_sA$ for prophylactic applications is the same as the above-described effective amounts for preventing platelet aggregation in vivo at the site of a pre-existing thrombus.

The utility of $Ap_spCHClpp_sA$ for modulating the above-described thrombolytic events is supported by the established utilities of the normally-occurring $AP_4A$ molecule in vivo. For example, $AP_4A$ has been shown to inhibit markedly ADP-induced platelet aggregation when it is administered to a mammal. Added before or during aggregation, exogenous $AP_4A$ causes rapid dispersion of aggregated platelets with the magnitude of inhibition bearing a direct relationship to the dose of exogenous $AP_4A$. Because platelet plugs form the bulk of arterial thrombi, a preferred therapeutic strategy to prevent thrombosis is consistent with the above-described administration of $Ap_spCHClpp_sA$ to a mammal to interfere with the adherence of platelets to each other in vivo. Thus, the utility of $Ap_spCHClpp_sA$ for modulating thrombolytic events in vivo is based upon scientific certainty that the naturally-occurring parent molecule, $AP_4A$ and an analogue, AppCHClppA inhibit thrombus formation when clinically administered to a mammal.

Surprisingly, $Ap_spCHClpp_sA$ advantageously offers increased platelet aggregation inhibitory properties compared to those of the normally-occurring $AP_4A$ or previously described $AP_4A$ analogs. These properties are unexpected and could not have been predicted based upon structural similarities to the analogs of naturally-occurring $AP_4A$ molecules. The significant differences in the inhibitory activity of $Ap_spCHClpp_sA$ compared to a known $AP_4A$ analog is illustrated in the accompanying Examples, which are not to be taken as limiting in any way.

EXAMPLES

Unless otherwise provided below, the experimental procedures were performed according to the procedures provided in U.S. Pat. No. 5,049.550 (Zamecnik '550), the entire contents of which are incorporated herein by reference. Some alternative procedures (e.g., release reaction, PF3 assays) and a number of additional studies also are provided (e.g., cytoplasmic calcium mobilization, fibrinogen binding site, agonists other than ADP, platelet cAMP and distribution of $CHCl-AP_4A$ into blood components). Blood was collected in a 0.1 volume of 3.8% sodium citrate from healthy human volunteers who had abstained from antiplatelet agents for at least 10 days. Platelet rich plasma (PRP) was separated by a gradual centrifugation and adjusted to $3.3\times 10^8$ platelets per ml plasma. PRP has been utilized in the Examples unless otherwise stated.

Throughout this document, $P^1$, $P^4$-dithio $P^2$, $P^3$-monochloromethylene 5', 5'''-diadenonsine $P^1$, $P^4$-tetraphosphate is referred to alternatively as "thio-CHCl-$AP_4A$" or "$Ap_spCHClpp_sA$."

EXAMPLE 1

Synthesis of $Ap_spCHClpp_sA$.

The synthesis of $Ap_spCHClpp_sA$ was performed in the laboratory of Professor M. Blackburn, University of Sheffield, England, and involved two steps. First, the ($p_\alpha$)-bisthio-analogue was prepared through the activation of adenosine 5'-thiomonophosphate with diphenylphosphochloridate and then proceeded to the condensation of adenosine 5'-thiomonophosphate with monochloromethylene bisphosphate (Blackburn, G. M. et al. *Nucl. Acids Res.* 15:6991–7004, (1987)). See also, *$AP_4A$ and Other Dinucleoside Polyphosphates*, ed. A. McLennan, CRC Press Inc. (1992), chapter 11 entitled "Synthetic Structural Analogues of Dinucleoside Polyphosphates" by G. M. Blackburn, et al. The product after chromatography on DEAE sepharose was 90% pure by $^{31}P$ NMR. Analytical purification using reverse phase HPLC provided material that was 99% pure and resolved the four stereoisomers, e.g. ApspCHClppsA, ApspCHClppa, AppCHClppsA and AppCHClppA. Further purification of the stereoisomers was not done.

EXAMPLE 2

Characterization of $Ap_sCHClpp_sA$

Results

I. Inhibition Potency of thio-CHCl-$AP_4A$ on ADP-induced Platelet Aggregation

An initial screening was performed for inhibitory effects of several agents (including, e.g., thio-CHCl-$AP_4A$ and CHCl-$AP_4A$ as reference agent)) on platelet aggregation induced by ADP. Platelet aggregation was measured with platelet-rich plasma (PKP) by the turbidimetric method of Born (*J. Physiol.* 162:67, 1962) in an aggregometer (Chrono-log, Model 530 VS). Platelet aggregation induced by 5 µM ADP in the absence or presence of 5 µM agents was examined. The study was extended to estimate the $IC_{50}$ values for each agent by performing a dose-dependent inhibition assay as demonstrated previously (P. Zamecnik et al., *Proc. Nat'l. Acad. Sci. USA* 89:2370–2373 (1992)). The results are summarized in Table 1. The $IC_{50}$ value of the CHCl-$AP_4A$ (reference agent) was consistent with the value reported previously (P. Zamecnik et al., *Proc. Nat'l. Acad. Sci. USA* 89:2370–2373 (1992)). The value of thio-CHCl-$AP_4A$ appeared the lowest (0.81 µM) among the agents tested, indicating the highest inhibitory potency. When both adenosine molecules of thio-CHCl-$AP_4A$ were replaced with deoxyadenosine (thio-CHCl-$dAP_4dA$), the inhibitory potency was significantly reduced (9.22 µM). Similarly, replacement with deoxyadenosine in the non-thiophosphonate compound (CHCl-$dAP_4dA$) resulted in complete loss of inhibitory effects (>100 µM). An inhibition kinetic study for thio-CHCl-AP$_4$A was performed as demonstrated previously for CHCl-AP$_4$A (P. Zamecnik et al., *PNAS (USA)* 89:2370–2373 (1992). The inhibition constant (Ki) value of thio-CHCl-AP$_4$A was 0.33 µM and exhibited competitive inhibition indicating the same nature but a higher potency than that of the CHCl-AP$_4$A (1.1 µM), reference agent.

TABLE 1

| Inhibitors | IC$_{50}$ (µM) |
|---|---|
| AppCHClppA (CHCl-AP$_4$A) | 3.28* |
| Ap$_S$pCHClpp$_S$A (Thio-CHCl-AP$_4$A) | 0.81* |
| dAppCHClppdA (CHCl-dAP$_4$dA) | >100 |
| dAp$^S$pCHClpp$^S$dA (Thio-CHCl-dAP$_4$dA | 9.22 |

*Mean values of three determinations; others are the mean of two determinations.

II. Effects of Thio-CHCl-AP$_4$A and CHCl-AP$_4$A on Platelet Responses other than Aggregation Platelet responses to the agonists include in addition to aggregation a) release reaction, b) fibrinogen receptor silos (GPIIb/IIIa) and, c) platelet factor 3 activation. The effects of thio-CHCl-AP$_4$A and the reference agent (CHCl-AP$_4$A, compound E$_{10}$ of Zamecnik '550) were tested on each of these responses.

a) Platelet Release Reaction

The effects of thio-CHCl-AP$_4$A and the reference agent on both ADP and collagen induced platelet aggregation, and release reaction were tested in a lumiaggregometer. Normal human PRP was separated from sodium titrate anticoagulated (0.38%) blood. Platelet aggregation and release reaction induced by 5 µM ADP or 1 µg collagen/ml. The lumiaggregometer was equipped to assay both platelet aggregation and the luciferase reaction of ATP simultaneously a) in the absence of agent (control); and b) in the presence of various concentrations of thio-CHCl-AP$_4$A or CHCl-AP$_4$A. The measured amount of ATP released from the activated platelets by the agonist represents the release reaction. The luminescence produced by the luciferin-luciferase reaction was linear with respect to the amount of ATP released.

The results are summarized in Table 2. The values of IC$_{50}$ in inhibitory effects on the release reaction, in general, are lower than that of aggregation, indicating that the inhibitory effects of the agents (thio-CHCl-AP$_4$A and CHCl-AP$_4$A) on the release reaction predominates over the inhibitory effects of these agents on aggregation. Collagen-induced aggregation was not inhibited by CHCl-AP$_4$A, however, the release reaction was inhibited by CHCl-AP$_4$A.

TABLE 2

| Agonists | Assays | CHCl-AP$_4$A (µM) | Thio-CHCl-AP$_4$A (µM) |
|---|---|---|---|
| ADP | Aggregation | 14 | 1.6 |
|  | Release Reaction | 4.5 | 0.7 |
| Collagen | Aggregation | >100 | 9.0 |
|  | Release Reaction | 35.0 | 1.7 | b) Fibrinogen Binding Sites (GPIIMIIIa) on the Platelets

Platelet surface receptors for fibrinogen are known to be increased by activation. The effects of thio-CHCl-AP$_4$A and CHCl-AP$_4$A on fibrinogen binding sites of activated platelets were assayed by means of Fluorescein isothiocyanate conjugated antifibrinogen antibody (FITC-anti-fgn) techniques in a flow cytometer (FACS, Becton-Dickinson). PRP was used at 1:20 final dilution. Platelets were activated by ADP in the presence or absence of the agents at 22° C. for 5 min. After incubation of activated platelets with FITC-Anti-Fgn at 22° C. for 10 min., 0.5 ml of 0.2% formyl saline (0.2% formaldehyde in 0.9% NaCl) was added to inhibit further activation. Samples included platelets that were a) unstimulated; b) stimulated with 5 µM ADP; c) exposed to agents (CHCl-AP$_4$A or thio-CHCl-AP$_4$A) for 5 minutes before ADP stimulation. Fibrinogen bound on the ADP-activated platelets was inhibited preferentially by thio-CHCl-AP$_4$A as compared to that of the reference agent, CHCl-AP$_4$A (Table 3).

TABLE 3

| Concentration of Agent (µM) | CHCl-AP$_4$A (% binding) | Thio-CHCl-AP$_4$A (% binding) |
|---|---|---|
| 0 | 100 | 100 |
| 2.5 | 70.9 | 9.9 |
| 5.0 | 41.3 | 5.3 |
| 7.5 | 36.1 | n.d. |
| 10 | 23.8 | n.d. | c) Platelet Factor 3 (PF3) Activation

PF3 activity of the platelets is enhanced by ADP stimulation and measured by the Stypven clotting time (P. Zamecnik et al., *PNAS (USA)* 89:2370–2373 (1992)). Table 4 summarizes the results for the effects of the agents on ADP-stimulated PF3 activity. The data represent a mean of two experiments. Fresh normal human platelet-rich plasma (3×10$^8$ platelets per ml) was preincubated in the presence or absence of the agents (10 µM) at 37° C. for 5 min and then tested for PF$_3$ activity of the platelets that was stimulated by 10 µM ADP. The inhibitory effect of thio-CHCl-AP$_4$A was significantly greater than that of the non-thio reference agent (CHCl-AP$_4$A).

TABLE 4

|  | Baseline Value | Saline Control | CHCl-AP$_4$A | Thio-CHCl-AP$_4$A |
|---|---|---|---|---|
| Clotting Time (sec.) | 45.8 | 38.9 | 43.1 | 44.5 |
| Net Change | — | −6.9 | −2.7 | −1.3 |
| % Change | — | 100 | 39.1 | 18.8 |

III. Effects of Thio-CHCl-AP$_4$A and CHCl-AP$_4$A on the Regulatory Factors in ADP-Induced Platelet Activation Three regulatory factors in the processes of platelet activation are known: a) cytoplasmic calcium ion mobilization, b) the changes in cellular cAMP levels, and c) arachidonic acid metabolic activity. The results for testing the agents (thio-CHCl-AP$_4$A and CHCl-AP$_4$A) for the first two of these factors are described below.

a) Cytoplasmic Calcium Ion (Ca$^{++}$) Mobilization

An increment of cytoplasmic Ca$^{++}$ in the platelets represents an activated state. Indo-1 acetomethyl ester (Indo-1) commonly has been utilized as the reagent to detect intracellular free Ca$^{++}$. Indo-1 reacts with Ca$^{++}$ and produces fluorescence which can be monitored in a dual wavelength (408/485) flow cytometer (Coulter EPIC Systems). Platelets were incubated with Indo-1 at 37° C. for 45 min. Excess Indo-1 in the medium was removed by gel-filtration method. Indo-1-loaded platelets were then activated by 6.7 µM ADP in the absence or presence of thio-CHCl-AP$_4$A (3.3 µM) or CHCl-AP$_4$A (6.7 µM). Fluorescence intensity of the platelets was monitored and plotted against platelet number. The histograms generated from the plots were analyzed. Unstimulated platelets registered fluorescence intensity (FI) between 42 and 250 with a peak at 133 (base line control). Platelets treated with 2 µM A23187 (a calcium ionosphere) showed a marked shift to the right (FI between 150 and 1,000) with a peak at 530) representing a positive control. ADP-activated platelets had a moderate shin to the right (FI between 67 and 300 with a peak at 158). The effect of ADP activation on $Ca^{++}$ mobilization was relatively mild compared to that of the calcium ionosphere and was blocked completely in the presence of either thio-CHCl-$AP_4A$ or CHCl-$AP_4A$, e.g. ADP-activated platelets in the presence of the inhibiting agent showed the same pattern as that obtained with unstimulated platelets.

b) Level of Intracellular cAMP

The inhibitory effect of cAMP on platelet aggregation has been known as a counteraction of calcium ion mobilization. Accordingly, the inhibitory effects of the agents with respect to a cAMP mediated mechanism was tested. PRP was incubated with saline (control), agents (at 20 µM and 100 µM), or forskolin (10 µM) at 37° C. for 5 min. After incubation, extracts were made using $Ba(OH)_2$ and $ZnSO_4$. Cyclic AMP in the extracts was converted into the etheno-cAMP derivative, and the levels were estimated by HPLC using a fluorescence detector (W. Wojcik et al., *J. Cyclic Nucleotide Res.* 7:27–35 (1981)). The level of cAMP in an unknown extract was determined by extrapolation from a standard graph. A linear relationship between the cAMP level in the extracted samples and fluorescence detection was observed. Table 5 shows the results of the agents' effect on the platelet cAMP level. Both thio-CHCl-$AP_4A$ and CHCl-$AP_4A$ showed no effect on the cAMP level at 20 µM, but did show a moderate increase in the platelet cAMP level at a higher concentration (100 µM). However, this increase may not be a specific effect. Although adenosine contamination in the tested $AP_4A$ agents was not detected, it is possible that either cellular adenosine nucleotide metabolic products or contaminated adenosine in the tested agents may be responsible for the elevated cAMP level. A marked increase in platelet cAMP by 101 µM forskolin, a potent stimulator for adenylate cyclase, was demonstrated for a positive control. These results suggest that the inhibitory effect of the agents on platelet activation by ADP may not follow a cAMP mediated mechanism.

TABLE 5

| Concentration of Agent (µM) | CHCl-$AP_4A$ (nM) | Thio-CHCl-$AP_4A$ (nM) | Forskolin (nM) |
| --- | --- | --- | --- |
| 0 | 31.6 | 31.6 | 31.6 |
| 10 | not done | not done | 124.4 |
| 20 | 30.6 | 28.6 | not done |
| 100 | 56.7 | 54.4 | not done |

IV. Effects of Thio-CHCl-$AP_4A$ and CHCl-$AP_4A$ on Platelet Aggregation Induced by Agonists Other Than ADP The release reaction appears to be a unique response following platelet activation. ADP, among several platelet constituents, appears to play an important role in the enhancement of activation. We have examined the role of ADP that is released in platelet aggregation induced by other agonists including arachidonic acid, collagen, epinephrine, thrombin and ristocetin. Platelet aggregability induced by a given concentration of agonists was approximately 60–80% in absence of agents. The values of $IC_{50}$ were estimated by a dose-dependent inhibition study with a varied concentration of CHCl-$AP_4A$ and thio-CHCl-$AP_4A$. Neither thio-CHCl-$AP_4A$ nor CHCl-$AP_4A$ affected thrombin and ristocetin-induced platelet aggregation. The values of inhibitory potency ($IC_{50}$) for the other three agonists are summarized in Table 6. Although collagen-induced aggregation appears to be unaffected by CHCl-$AP_4A$, a detectable inhibitory effect was noted for thio-CHCl-$AP_4A$. These results suggest that at least 50% of platelet aggregability induced by arachidonic acid, collagen or epinephrine is dependent upon ADP being released from the initial platelet activation. This finding supports the above-described observations of the inhibitory effects of the agents on the release reaction.

TABLE 6

| Agonists | CHCl-$AP_4A$ (µM) | Thio-CHCl-$AP_4A$ (µM) |
| --- | --- | --- |
| ADP (5 µM) | 3.28 | 0.81 |
| Arachidonic Acid (1 mM) | 19.0 | 9.12 |
| Collagen (µg) | >100 | 9.00 |
| Epinephrine (10 µM) | 24.0 | 5.25 |

V. Ability to Aggregate of the Platelets Exposed Previously to Thio-CHCl-$AP_4A$ and CHCl-$AP_4A$ Platelets possess the purinoceptor ($P_{2T}$), a specific binding site for ADP on the platelet surface. We believe that the inhibition mechanism of $AP_4A$ analogues involves competing with ADP for binding to the platelet purinoceptor. To test the stability and inhibitory effects of the bound agent, platelet-rich plasma anticoagulated with ACD solution was preincubated with 25 µM thio-CHCl-$AP_4A$ or 50 µM CHCl-$AP_4A$ at 22° C. for 30 minutes. Platelets isolated by gel-column filtration ($2\times10^8$ cells/ml) or centrifugation ($3\times10^8$ cells/ml) were resuspended in the inhibitor-free plasma and ADP-induced aggregability was measured. The values represent a mean of three experiments for the series of gel-filtration separation and a mean of two experiments for the centrifugation separation. Table 7 summarizes the results. Platelets exposed to thio-CHCl-$AP_4A$ showed a moderate inhibition in the ability to aggregate following exposure to ADP (22–33%), while CHCl-$AP_4A$ exposed platelets exhibited only a slight inhibition effect (8%). The results suggest that the inhibitory activities of the $AP_4A$ analogues which bound to the platelets apparently are reversible.

TABLE 7

| Method of Separation | Concentration of ADP | Inhibiting Agent | Aggregability (% of control) |
| --- | --- | --- | --- |
| Gel-Filtration | 10 µM | None | 100 |
| | 10 µM | Thio-CHCl-$AP_4A$ | 78 |
| | 20 µM | None | 100 |
| Centrifugation | 20 µM | Thio-CHCl-$AP_4A$ | 67 |
| | 20 µM | CHCl-$AP_4A$ | 92 |

VI. Time-Dependent Effects of Thio-CHCl-$AP_4A$ and CHCl-$AP_4A$ on ADP-Induced Aggregation To observe the stability of the agents by functional assay, PRP was incubated with 2.51 µM thio-CHCl-$AP_4A$ or 5 µM CHCl-$AP_4A$ at 37° C. for 3 hours. The concentrations of inhibiting agents used in this experiment were relatively low, especially for the thio compound. Samples taken at the times indicated were tested for ADP-induced (10 µM) aggregation. The results are summarized in Table 8. Inhibitory effect of thio-CHCl-$AP_4A$ was well-retained for up to 3 hours, while the effects of CHCl-$AP_4A$ gradually decreased with prolonged incubation time. The results suggest that CHCl-$AP_4A$ becomes unstable when it is kept in PRP more than 60 minutes at 37° C. and that thio-CHCl-AP$_4$A is very stable for at least a 3 hour period. A similar stability of thio-CHCl-AP$_4$A was observed in the whole blood incubation.

TABLE 8

| Incubation Time (min) | Absence of Inhibiting Agent | Presence of Inhibiting Agent | |
|---|---|---|---|
| | | CHCl-Ap$_4$A (5 μM) | Thio-CHCl-AP$_4$A (2.5 μM) |
| 0 | 82% | 13% | 21% |
| 60 | 69% | 31% | 7% |
| 120 | 59% | 47% | 5% |
| 180 | 43% | 42% | 6% |

VII. Heat Stability of Thio-CHCl-AP$_4$A and CHCl-AP$_4$A

Both agents were heated at the boiling temperature. Samples were taken at 5, 15, and 30 minutes. The inhibitory effects on platelet aggregability and physical integrity of the agents assayed by HPLC showed no changes, indicating both agents are resistant to heat treatment for up to 30 minutes.

VIII. Stability of Thio-CHCl-AP$_4$A and AP$_4$A in Whole Blood

To test the molecular stability of the agents, blood was incubated with each agent at 370° C. for 4 hours. Samplings at the indicated incubation times were extracted and CHC -AP$_4$A or thio-CHCl-AP$_4$A were assayed in an HPLC (Waters 600E pump and controller) with quartenary amine anion exchange column (Whatman Partisil 10) and analysed (Beckman System Gold). The retention times for CHCl-AP$_4$A and thio-CHCl-AP$_4$A were 3.39 and 5.95, respectively. Peak areas were integrated and used to construct a standard curve for a concentration range (1, 2, 4, 6, 8 and 10 μM). Both CHCl-AP$_4$A and thio-CHCl-AP$_4$A were pure, as observed by a single peak on HPLC, and by a linear relationship between the concentration of the agent and HPLC peak areas. Normal human blood anticoagulated with 0.38% sodium citrate was incubated in the presence of 250 μM CHCl-AP$_4$A or thio-CHCl-AP$_4$A at 370° C. for 4 hours. Blood samples were extracted with 3% perchloric acid and neutralized with K$_2$CO$_3$. The extracts were kept at −80° C. until an assay using an HPLC. The results for the blood extracts are summarized in Table 9. The values in Table 9 represent a mean of two experiments and are expressed in nmol/ml blood. We identified two peaks (major and second) from the blood extracts for CHCl-AP$_4$A or thio-CHCl-AP$_4$A. Total extraction efficiency shows 110% with CHCl-AP$_4$A at 60 minutes and 85% with thio-CHCl-AP$_4$A at 120 minutes. The apparent high value in the extraction efficiency of CHCl-AP$_4$A suggests that blood-borne adenosine compounds (possible adenosine and AMP) may contribute to the major peak. An estimated quantity of CHCl-AP$_4$A major peak indicated a slow degradation showing a reduction of 30% after 4 hours incubation. At least 80% of degradation product, possibly chloromethylene monoadenosine triphosphate (AppCp) is associated with the second peak (X1). Extraction efficiency of thio-CHCl-AP$_4$A was relatively poor (69%) at time 0 but showed an improvement (81–85%), and became closer to each other between samples after 60 minutes. The data indicate that the thio derivative is, in general, very stable in blood for at least 4 hours at 37° C. The second peak of the blood extract with thio-CHCl-AP$_4$A may be an isomer (X2), e.g., monothio compound (Ap$_s$pCppA or AppCpp$_s$A). It was not detected by HPLC of the pure compound, but registered a small portion (<10%) in the blood extraction at time 0 and about 20% of the major peak thereafter.

TABLE 9

| Incubation Time | CHCl-AP$_4$A | | | Thio-CHCl-AP$_4$A | | |
|---|---|---|---|---|---|---|
| (Minutes) | Main Peak | X1 | Total | Main Peak | X2 | Total |
| 0 | 249.2 | trace | 249.2 | 157.7 | 14.3 | 172.0 |
| 60 | 249.0 | 25.8 | 274.8 | 172.3 | 33.6 | 205.9 |
| 120 | 222.0 | 36.6 | 258.6 | 180.0 | 31.4 | 211.4 |
| 240 | 173.2 | 63.3 | 236.3 | 173.7 | 38.3 | 202.0 |

IX. Distribution of $^{125}$I-labeled CHCl-AP$_4$A into Different Blood Cell Fractions Platelets possess P$_{2T}$ purinoceptor, the specific sites for ADP and ATP (R. G. Humphries et al., *J. Cyclic Nucleotide Res.* 7:27–35 (1981)). There are, however, a variety of purinoceptors on other cell types. AP$_4$A analogues may bind not only to platelets but also to the erythrocytes and leukocytes when whole blood is treated with the agents. We have found that all three cell fractions are indeed associated with CHCl-AP$_4$A. In our study, human blood was incubated with 23 μM CHCl-AP$_4$A containing a trace mount of $^{125}$I-CHCl-AP$_4$A (specific activity of ~35 μ Ci/μMol, and a gift from Dr. David Elmaleh, Radiology Department, Massachusetts General Hospital, Boston, Mass.) at 22° C. for 30 minutes. Platelets were separated by a gradual centrifugation, the packed red cells with buffy coats (leukocytes) were mixed, and fractionated by means of histopaque gradient separation (A. Boyum, *Scand J. Clin. Lab. Invest.* 21(suppl 97):77 (1968)). The cell fractions were washed twice and final suspensions were counted for cell number and the radioactivity. Percent distribution was calculated based on the CBC data of whole blood. The results (a mean of two determinations) are summarized in Table 10. Binding sites are expressed in the values per cells.

TABLE 10

| Components | Distribution (%) | Binding Sites |
|---|---|---|
| Erythrocytes | 2.09 | $5.98 \times 10^4$ |
| Leukocytes | 1.94 | $7.39 \times 10^7$ |
| Platelets | 0.55 | $3.08 \times 10^5$ |
| Plasma & Washes | 95.5 | — |

All three cell fractions were associated with the radioactivity, indicating the CHCl-AP$_4$A binds to multiple blood cell types. A comparison between the cell types and distribution data enabled us to calculate a gross estimation of binding sites per cell. Platelets appeared to have higher (one log) binding sites per cell compared to erythrocytes, although the size of platelets is less than one tenth that of erythrocytes. On the other hand, the binding sites per cell was two logs higher in leukocytes compared to that observed for platelets. The results suggest that the binding sites for CHCl-AP$_4$A per surface area of the cells exhibit a relative value of $10^3$, $10^2$ and 1 on the leukocytes, platelets and erythrocytes, respectively.

EXAMPLE 3

Further Characterization of Thio-CHCl-AP$_4$A

1. Pharmacokinetics & Pharmacodynamics

General Protocol

The same rabbit model that has been reported previously (S. Louie et.al., *Thromb. Res.* 49:557–565 (1988); B. K. Kim et al., *Proc. Nat'l. Acad. Sci. USA* 89:11056–11058 (1992)) is used in this example. This rabbit model is considered by those skilled in the art to be predictive with respect to the effects of the tested agents in humans and is useful for selecting the dosage ranges of the agents for administration to humans. To avoid possible bias by minor changes in surgical technique, all the animal work is performed by the same operator, with the rabbits assigned to experimental or control groups at random.

Male, New Zealand white rabbits, weighing 2–2.5 kg., are infused with thio-CHCl-AP$_4$A at a dose indicated by a bolus or continuously for 2 hr via a marginal ear vein. Blood is sampled from the artery of the ear with 1/10 volume of 3.8% sodium citrate at indicated time post-infusion. Immediately after blood samplings, microvascular bleeding time is determined (Mielke, C. H., Thromb. Haemostasis 52:210–211 (1984)). An aliquot of blood is extracted with perchloric acid for HPLC assay of the agent. Whole blood platelet aggregation by ADP is assayed for all blood samples. The results provide preliminary information on the effective dose as well as the effective time period.

After preliminary trials with continuous infusion or bolus infusion, a standard thio-CHCl-AP$_4$A infusion protocol is established as follows. Three different doses, 0.5×, 1× and 2× dose are tested for their antithrombotic effect in the rabbit intracarotid carmula thrombosis model at the time indicated in the specific protocol (S. Louie et.al., *Thromb. Res.* 49:557–565 (1988); B. K. Kim et al., *Proc. Nat'l. Acad. Sci. USA* 89:11056–11058 (1992)). A dose of thio-CHCl-AP$_4$A is reconstituted in 10 ml of normal saline and infused by pump at a uniform rate or by bolus infusion. Control rabbits receive 10 ml of saline alone. A segment of common carotid artery is isolated by use of vascular clamps in the anesthetized rabbit. The cannula is inserted, and the re-establishment of blood flow is timed at 15 min. Upon the completion of infusion, or 1 hr after bolus infusion, the intracarotid tubing is removed, and its contents flushed out into a petri dish. The presence of a clot or of liquid blood contents is noted. The incidence of clot formation in the intracarotid cannula in the different groups is compared by the Chi-Square test.

Assay of Blood thio-CHCl-AP$_4$A

Blood samples are collected from the opposite side carotid artery or the ear artery before and after (0, 10, 20, 40, 60 and 120 min.) infusion of thio-CHCl-AP$_4$A. Blood is anticoagulated by mixing with 1/10 volume of acid-citrate-dextrose solution. Blood samples are extracted with perchloric acid, centrifuged, and the acid soluble fraction neutralized by 5M K$_2$CO$_3$ (S. Louie et.al., *Thromb. Res.* 49:557–565 (1988)). The samples are kept at −80° C. until assay of the nucleotides by HPLC.

Platelet Aggregation Studies

A Chrono-log whole-blood platelet aggregometer (Model 530 VS) equipped with a recorder is used for the measurement of platelet aggregation as described in Example 1.

Microvascular Bleeding Time Study

A Simplate bleeding-time device is used (Organon Teknika). After shaving the dorsal surface of the ear, the site is carefully selected under an illuminator to avoid gross vasculature. Bleeding time is measured under free flow, devoid of pressure. The unpaired t-test is used to compare the prolongation of bleeding time in the different groups.

Carotid Artery Cannula Thrombosis Model

The rabbits are anesthethized with ketamine hydrochloride (100 mg/kg i.m.). A segment of the left common carotid artery is isolated by vascular clamps. A 1 cm length of polyethylene tubing (1-mm i.d.; intramedic polyethylene tubing PE-90, Clay Adams, Parsippany, N.Y.) is inserted, secured by silk ligatures, and the blood flow re-established by removing the clamps.

Specific Protocol a) Dose and time-dependent effects on platelet aggregation

A series of four different dose and time intervals for the inhibitory effects on ADP-induced platelet aggregation is studied. Rabbits, approximately 2.5 kg, are infused intravenously with a single bolus dose of the agent at: 5, 10, 20, 40 and 100 mg/kg. Blood samples are collected before infusion, 30 min, 2 hr, 6 hr, 24 hr and 48 hr (if necessary) post-infusion. Immediately after blood samplings, microvascular bleeding time is determined. Whole blood platelet aggregation by ADP is assayed for all blood samples (B. K. Kim et at., *Proc. Nat'l. Acad. Sci. USA* 89: 11056–11058 (1992)).

The results indicate the effective dose as well as effective time interval. Preferably, six rabbits are used at each dose study and the total number of rabbits required is twenty-four rabbits.

b) Antithrombotic effects

Based on the preceding study, three different doses, 0.5×, 1× and 2× effective dose (ED) are tested for their antithrombotic effect in rabbit intracarotid cannula thrombosis model (S. Louie et.al., *Thromb Res.* 49:557–565 (1988); B. K. Kim et at., *Proc. Nat'l. Acad. Sci.* 89: 11056–11058 (1992)) at effective time (ET) x1, x2, x4, after infusion of the agent. Preferably, fifteen rabbits are used at each dose study and the total number of rabbits required is 150 rabbits.

c) Double blind efficacy study

An effective dose is chosen based on the preceding study and a double blind study is performed using the same protocol as described in the above section. Rabbit, ID# assigned randomly, is infused with saline solution that contains none or an effective dose of the agent without disclosure to the investigator until the completion of the study.

Preferably, fifteen rabbits are used for each group (with or without agent) and the total number of rabbits required is 30 rabbits. The incidence of clot formation in the intracarotid cannula in the two groups is compared by the Chi-Square test.

d) Study on biodistribution and clearance time of the agent

Thio-CHCl-AP$_4$A has been labeled with $^{125}$I by Dr. David Elmaleh (Radiology Department, Massachusetts General Hospital, Boston, Mass.), or by a commercial labeling service. The biodistribution of [$^{125}$I]-thio-CHCl-AP$_4$A is studied in two groups of three rabbits. 2–5 μCi of agent in 0.2 ml of saline is injected intravenously in one ear vein of the rabbits. Blood samples are taken from the other ear artery at 5, 10, 20, 40 and 90 min after injection, followed by sacrificing the animal with pentobarbital (150 mg/kg). The major organs, e.g., blood, kidney, liver, lungs, spleen, brain, thyroid, muscle and bone, as well as the urine aspirated from the bladder are collected and weighed. Tissues or organs are cut into smaller pieces, weighed and placed in scintillation vials and assayed for $^{125}$I. The percent injected dose per organ is calculated.

e) Method of Administration, Route and Frequency

Phosphodiester forms of AP$_4$A analogues do not cross the external cell membrane (P. C. Zamecnik and M. L. Stephenson in H. M. Kalckar et al., eds., *Alfred Benzon Symposium,*

I, 276–291, Munksgaard, Copenhagen (1968)). However, a recent study has indicated that the thionation of the oligodeoxynucleotides greatly enhanced their antiviral effectiveness (Leiter, J. M. E, et al., *Proc. Nat'l. Acad. Sci. USA* 87:3430–3434 (1990); Agrawal, S., et al., *Proc. Nat'l. Acad. Sci. USA* 85:7079–7083 (1988); Zamecnik, P. C., et al., *In AIDS Res. Reviews* Vol I, Koff, W. C. et al, (Eds) Marcel Dekker, Inc., NY, 301–313 (1991); Matsukura, M. *In Antisense Res. and Applications*; Crooke, S. T., et al., (Eds) *CRC Press.*, NY 505–520 (1993). This suggested to us the possibility that thio-CHCl-AP$_4$A may be suitable for administration by ingestion.

The blood levels of the agent after administration through a gastric catheter in anesthetized rabbits are determined. After anesthetization, a gastric catheter is inserted through the mouth and a desired dose of the agent is administered. Blood samples are drawn at 10, 30, 60, 120, 240 and 360 min after administration of the agent. Blood samples are monitored for whole blood platelet aggregation (Cardinal, D. C. and Flower, R. J., *J. Pharmacol. Method* 3:135–158 (1980)). The agent is extracted and its level in blood is determined by HPLC. Repeated doses at a desired frequency are administered to the mammal to maintain a blood level of the agent that is effective for antiplatelet activity.

Preferably, six rabbits are used for this study. The results from this experiment are used to better define the parameters for an oral route of administration.

2. Toxicity and safety of the agent

Animal toxicity studies are conducted after the successful completion of the above-described pharmacology studies in accordance with standard procedures. Preferably, two animal species, rabbits and pigs are selected for the toxicity studies. These are established animal species for toxicology studies, and are accepted for such studies by the appropriate regulatory agencies. Animal toxicity studies are carried out in a GLP facility (TSI Mason Laboratories/Genzyme Corp., Worcester, Mass.) in accordance with standard practice. Typically, the acute toxicity studies involve two parts: (1) a range finding study to establish the tolerated dose range and (2) an acute toxicity study to establish the maximum tolerated dose. Acute toxicity studies are followed by chronic toxicity studies to induce functional and/or morphological changes in animals by repeatedly dosing the animals at several dose levels (including at an expected toxic level). The chronic toxicity testing is performed to identify target organs where adverse side effects might be expected to occur. During the course of the study, animals are observed for changes in physical appearance and clinical behavior, body weight gain and food and water consumption. Ophthalmological examination, cardiovascular and other physiological parameters are measured or monitored where practical; All major organs and tissues are examined histopathologically.

Acute toxicity testing on a drug generally constitutes the first step in assessing its toxicity potential. The purpose of an acute toxicity test is to define the adverse effects and, if possible, the lethality of the agent when administered one time only at relatively high dosages. If present, overt signs of toxicity produced at one or more dose levels are noted and the median lethal dose is estimated if deaths occur at more than one dose level.

Each of the patents, patent publications, references and other documents identified herein is incorporated in its entirety herein by reference.

It should be understood that the preceding description and the following Examples are merely a detailed description of certain preferred embodiments. It therefore should be apparent to those skilled in the art that various modifications and equivalents can be made without departing from the spirit or scope of the invention.

What is claimed is:

1. A composition comprising: $P^1$, $P_4$-dithio-$P^2$, $P^3$-monochloromethylene 5', 5'''diadenosine $P^1$, $P^4$-tetraphosphate.

2. The composition of claim 1, wherein $P^1$, $P^4$-dithio-$P^2$, $P^3$-monochloromethylene 5', 5'''-diadenosine $P^1$, $P^4$-tetraphosphate is present in an effective antithrombotic mount, the composition further comprising a pharmaceutically acceptable carrier.

3. The composition of claim 1, wherein the effective antithrombotic amount is between 1 mg and 25 mg per kg body weight per day.

4. The composition of claim 2, further comprising a thrombolytic amount of at least one thrombolytic agent.

5. The composition of claim 4, wherein the thrombolytic agent is selected from the group consisting of tissue plasminogen activator, streptokinase and urokinase.

6. The composition of claim 3, further comprising a thrombolytic amount of at least one thrombolytic agent.

7. The composition of claim 6, wherein the thrombolytic agent is selected from the group consisting of tissue plasminogen activator, streptokinase and urokinase.

8. A method for modulating a thrombolytic effect in a mammal in need thereof, the method comprising, administering to the mammal a pharmaceutical composition containing an effective antithrombotic amount of $P^1$, $P^4$-dithio-$P^2$, $P^3$-monochlormethylene 5', 5'''-diadenosine $P^1$, $P^4$-tetraphosphate to modulate the thrombolytic effect.

9. The method of claim 8, wherein the effective antithrombotic amount is between 1 mg and 25 mg per kg body weight per day.

10. The method of claim 8, wherein modulating a thrombolytic effect comprises facilitating dissolution of a thrombus in the mammal and the effective amount of $P^1$, $P^4$-dithio-$P^2$, $P^3$-monochloromethylene 5', 5'''-diadenosine $P^1$, $P^4$-tetraphosphate to modulate the thrombolytic effect is an effective antithrombotic amount, the method further comprising administering to the mammal an effective thrombolytic amount of a thrombolytic agent.

11. The method of claim 10, wherein the thrombolytic agent is selected from the group consisting of tissue plasminogen activator, streptokinase and urokinase.

12. The method of claim 8, wherein modulating a thrombolytic effect comprises inhibiting platelet aggregation in the mammal and the effective mount of $P^1$, $P^4$-dithio-$P^2$, $P^3$-monochloromethylene 5', 5'''-diadenosine $P^1$, $P^4$-tetraphosphate is an amount effective for inhibiting platelet aggregation in vivo.

13. A pharmaceutical composition comprising, $P^1$, $P^{4\text{-}dithio\text{-}P2}$, $P^3$-monochloromethylene 5', 5'''-diadenosine $P^1$, $P^4$-tetraphosphate, and a pharmaceutically-acceptable carrier.

14. The composition of claim 13, wherein the composition is formulated to contain a single dose for administration to a mammal.

* * * * *

UNITED STATES PATENT AND TRADEMARK OFFICE
CERTIFICATE OF CORRECTION

PATENT NO. : 5,681,823

DATED : October 28, 1997

INVENTOR(S) : Byung K. Kim, Paul C. Zamecnik

It is certified that error appears in the above-identified patent and that said Letters Patent is hereby corrected as shown below:

Column 1, line 54 please change "et at." to --et al.--.
Column 1, line 54 please change "*Haemost.*" to --*Haemostas*--.
Column 2, line 29 please change "In vitro" to --*In vitro*--.
Column 2, line 51 please change "Zamecrdk" to --Zamecnik--.
Column 4, line 19 please change "in vivo" to --*in vivo*--.
Column 4, line 38 please change "in vitro" to --*in vitro*--.
Column 4, line 42 please change "$E_3$" to --$E_{13}$--.
Column 4, line 54 please change "$ID_{10}$" to --$ID_{50}$--.
Column 5, line 56 please change "bull" to --bulk--.
Column 6, line 26 please change "in vive" to --*in vivo*--.
Column 6, line 27 please change "ex vive" to --*ex vivo*--.
Column 6, line 28 please change "in vive" to --*in vivo*--.
Column 6, line 28-29 please change "ex vivo" to --*ex vivo*--.
Column 6, line 30 please change "titrated" to --citrated--.
Column 7, line 17 please change "in vivo" to --*in vivo*--.
Column 7, line 20 please change "in vivo" to --*in vivo*--.
Column 7, line 25 please change "in vivo" to --*in vivo*--.
Column 7, line 28 please change "in vivo" to --*in vivo*--.
Column 7, line 35 please change "in vivo" to --*in vivo*--.
Column 7, line 42 please change "in vivo" to --*in vivo*--.
Column 7, line 44 please change "in vivo" to --*in vivo*--.
Column 8, line 3 please change "drag" to --drug--.
Column 8, line 13 please change "in vivo" to --*in vivo*--.
Column 8, line 19 please change "drags" to --drugs--.
Column 8, line 21 please change "in vivo" to --*in vivo*--.
Column 8, line 39 please change "in vivo" to --*in vivo*--.
Column 8, line 66 please change "in vivo" to --*in vivo*--.
Column 9, line 10 please change "in vivo" to --*in vivo*--.
Column 9, line 13 please change "in vivo" to --*in vivo*--.
Column 9, line 29 please change "in vivo" to --*in vivo*--.
Column 9, line 33 please change "normally" to --naturally--.
Column 9, line 33-34 please change "in vivo" to --*in vivo*--.

UNITED STATES PATENT AND TRADEMARK OFFICE
CERTIFICATE OF CORRECTION

PATENT NO. : 5,681,823
DATED : October 28, 1997
INVENTOR(S) : Byung K. Kim, Paul C. Zamecnik It is certified that error appears in the above-identified patent and that said Letters Patent is hereby corrected as shown below:

Column 9, line 44 please change "in vivo" to --*in vivo*--.
Column 9, line 45 please change "in vivo" to --*in vivo*--.
Column 9, line 63 please change "5,049.550" to --5,049,550--.
Column 10, line 34 please change "ApspCHClppsA" to --Ap$_s$pCHClpp$_s$A--.
Column 10, line 34 please change "ApspCHClppa" to --Ap$_s$pCHClppA--.
Column 10, line 34 please change "AppCHClppsA" to --AppCHClpp$_s$A--.
Column 10, line 48 please change "(PKP)" to --(PRP)--.
Column 11, line 22 please change "silos" to --sites--.
Column 11, line 62 please change "GPIIMIIIa" to --GPIIb/IIIa--.
Column 13, line 6 please change "fight" to --right--.
Column 15, line 27 please change "370°C" to --37°C--.

IN THE CLAIMS:

Column 20, line 15 please change "mount" to --amount--.
Column 20, line 56 please change "in vivo" to --*in vivo*--.
Column 20, line 58 please change "P$^{4\text{-dithio-}}$P$^2$" to --P$^4$-dithio-P$^2$--.

Signed and Sealed this

Nineteenth Day of May, 1998

*Attest:*

BRUCE LEHMAN

*Attesting Officer*     *Commissioner of Patents and Trademarks*